(12) United States Patent
Umeki et al.

(10) Patent No.: US 10,570,019 B2
(45) Date of Patent: Feb. 25, 2020

(54) AMORPHOUS SILICON FOR USE IN FOODS, DRUGS, COSMETICS AND FEED, AND PRODUCTION METHOD AND PRODUCTION DEVICE THEREOF

(71) Applicant: GAIA Institute of Environmental Technology Inc., Miyagi (JP)

(72) Inventors: Senshin Umeki, Miyagi (JP); Nobukazu Taguchi, Miyagi (JP); Noriko Konma, Miyagi (JP)

(73) Assignee: GAIA Institute of Environment Technology Inc., Miyagi (JP)

(*) Notice: Subject to any disclaimer, the term of this patent is extended or adjusted under 35 U.S.C. 154(b) by 138 days.

(21) Appl. No.: 15/315,933

(22) PCT Filed: Jun. 3, 2015

(86) PCT No.: PCT/JP2015/066122
§ 371 (c)(1),
(2) Date: Dec. 29, 2016

(87) PCT Pub. No.: WO2015/186769
PCT Pub. Date: Dec. 10, 2015

(65) Prior Publication Data
US 2017/0158515 A1  Jun. 8, 2017

(30) Foreign Application Priority Data
Jun. 3, 2014 (JP) .................................. 2014-115197

(51) Int. Cl.
*C01B 33/021* (2006.01)
*C01B 33/18* (2006.01)
(Continued)

(52) U.S. Cl.
CPC ............ *C01B 33/021* (2013.01); *A23K 10/00* (2016.05); *A23K 20/20* (2016.05); *A23K 20/28* (2016.05);
(Continued)

(58) Field of Classification Search
CPC ...... F27B 7/08; F27B 7/10; F27B 7/18; F27B 7/20; F27B 7/33; F27B 7/36; F27B 7/42
See application file for complete search history.

(56) References Cited

U.S. PATENT DOCUMENTS

| 2009/0071409 A1 | 3/2009 | Ichige | |
|---|---|---|---|
| 2012/0041081 A1* | 2/2012 | Hammond | A61K 8/97 514/783 |

FOREIGN PATENT DOCUMENTS

| EP | 1217318 A1 * | 6/2002 | ............... C10B 7/10 |
|---|---|---|---|
| JP | 52-49573 | 11/1977 | |

(Continued)

OTHER PUBLICATIONS

International Search Report, PCT/JP2015/066122, dated Sep. 1, 2015.

*Primary Examiner* — Melvin C. Mayes
*Assistant Examiner* — Michael Forrest
(74) *Attorney, Agent, or Firm* — Young & Thompson (57) ABSTRACT

A porous and easy water soluble amorphous silica which does not contain tar, crystal, residual agrichemicals, and carcinogens, and method and apparatus to produce same, by using only one burning treatment from a plant including abundant silica, including a method of manufacturing the amorphous silica wherein rice family plants are burned while stirring and introducing into the furnace an atmospheric gas having a mass of 6.7× or more and 20× or less of the weight of the rice family plants, or oxygen gas having a weight of 1.4× or more and 4× or less with respect to the weight of the rice family plants, and at the same time as burning, combustion gas generated at the time of combustion is discharged.

3 Claims, 4 Drawing Sheets

(51) Int. Cl.
  *F27B 7/20* (2006.01)
  *F27B 7/08* (2006.01)
  *F27B 7/10* (2006.01)
  *F27B 7/18* (2006.01)
  *F27B 7/42* (2006.01)
  *F27B 7/33* (2006.01)
  *F27B 7/36* (2006.01)
  *A61K 8/25* (2006.01)
  *A61Q 19/00* (2006.01)
  *A23K 10/00* (2016.01)
  *A23K 20/20* (2016.01)
  *A23L 33/16* (2016.01)
  *A23K 20/28* (2016.01)
  *A23K 50/75* (2016.01)
  *A23K 50/00* (2016.01)
  *A61K 33/00* (2006.01)

(52) U.S. Cl.
  CPC .............. *A23K 50/00* (2016.05); *A23K 50/75* (2016.05); *A23L 33/16* (2016.08); *A61K 8/25* (2013.01); *A61K 33/00* (2013.01); *A61Q 19/00* (2013.01); *C01B 33/18* (2013.01); *F27B 7/08* (2013.01); *F27B 7/10* (2013.01); *F27B 7/18* (2013.01); *F27B 7/20* (2013.01); *F27B 7/33* (2013.01); *F27B 7/36* (2013.01); *F27B 7/42* (2013.01); *A23V 2002/00* (2013.01); *A61K 2800/10* (2013.01); *A61K 2800/522* (2013.01); *A61K 2800/805* (2013.01); *C01P 2002/02* (2013.01); *C01P 2006/80* (2013.01)

(56) References Cited

FOREIGN PATENT DOCUMENTS

| | | | |
|---|---|---|---|
| JP | 55-150418 | 11/1980 | |
| JP | 2002-130629 | 5/2002 | |
| JP | 2004-315389 | 11/2004 | |
| JP | 2008-214158 | 9/2008 | |
| JP | 2011-142826 | 7/2011 | |
| JP | 2011142826 | * 7/2011 | ............... A23L 1/00 |
| WO | WO 2006/051829 | 5/2006 | |
| WO | WO 2010/082442 | 7/2010 | |

* cited by examiner

FIG. 4 the present invention according to another embodiment
AMORPHOUS SILICON FOR USE IN FOODS, DRUGS, COSMETICS AND FEED, AND PRODUCTION METHOD AND PRODUCTION DEVICE THEREOF

TECHNICAL FIELD

The present invention relates to amorphous silica not containing tar, crystal and carcinogens which is porous and easily soluble in water and used for foods, medicines, cosmetics and feeds, a manufacturing method thereof and a manufacturing apparatus thereof.

BACKGROUND ART

Silica is a useful material for rice cultivation and the growth of some agricultural crops and has been used as silica fertilizer. In recent years, it has been pointed out that silica is an essential trace mineral not only for agricultural crops but also for the human body, and it has been pointed out that the value as food, medicine and cosmetics is increasing.

Silicon (Si) is 25.8% in Clarke number, and it is the second most frequent substance after oxygen on the earth. Silicon has a lot of its solid as silicon dioxide (SiO2), but most of it is "crystalline". On the other hand, silica that is absorbed by humans and animals and plants is "amorphous" silica, which is contained in diatomaceous earth, plants and the like. In addition, amorphous silica not containing crystalline silica is generally rare and expensive as crystalline silica has been pointed out as carcinogenic to human body.

Rice hulls and rice straw contain a large amount of amorphous silica. Many methods have been devised to obtain amorphous silica by burning rice husks and rice straw. In the conventional process for producing amorphous silica from rice hulls, in the case of obtaining rum hull combustion products, the rice husks are first fired in a fluidized bed burning furnace and then in an externally heated rotary oven a second firing There was a general way to create combustion products of shells.

PRIOR ART DOCUMENT

Patent Document

[Patent Document 1] Japanese Unexamined Patent Publication No. 2011-142826
[Patent Document 2] Japanese Unexamined Patent Publication No. 2006-112687
[Patent Document 3] JP-A-7-196312

DISCLOSURE OF THE INVENTION

Problem to be Solved by the Invention

In Patent Document 1, there is a problem that it is difficult to keep the furnace temperature constant, continuously and inexpensively and stably, and it is impossible to manufacture amorphous silica containing amorphous silica at a ratio nearly 100%. In addition, due to problems of dry distillation gas and tar generated during firing, there is a possibility that tar content may be mixed in the product, and it is difficult to use for foods, medicines, feeds, and the like.

In Patent Document 2, it states that "there is no local overheating generated in the firing course, so it does not include clinker grains (crystals) resulting from firing," in paragraph 0037, and as a result, paragraph 0038), it is stated that the amorphous silica porous body was obtained up to 40% although it varies depending on the test, and there is a problem that amorphous silica nearly 100% is not obtain. Amorphous silica is about half of amorphous silica.

In the manufacturing method of amorphous silica containing amorphous silica of Patent Document 3, two firing steps of primary firing and secondary firing are required, and there were the problem that the sintering process is complicated. In addition, regarding the use of amorphous silica containing amorphous silica, only the reinforcing material of concrete is disclosed. And foods, medicines, and feeds for which it is essential to contain no carcinogens, and foods, medicines, feeds for which it is essential to use water-soluble amorphous silica are not disclosed.

An object of the present invention is to provide an amorphous silica and a method and apparatus thereof which does not contain tar, crystals, residual agrichemicals and carcinogens, which is porous and readily soluble in water, and which is used for foods, medicine, cosmetics and feeds produced from rice husk, rice straw, rice bran, rice family plants such as wheat, corn, grass and the like, and plant which is rich in silica such as horsetailes, tea and potato etc. (hereinafter collectively referred to as "rice husks etc.") by only one process of a combustion treatment.

Means for Solving the Problem

The present invention according to one embodiment is, a method of manufacturing an amorphous silica which is porous and easily soluble in water and which does not contain tar, crystal, residual agrichemicals and carcinogens, which comprising, burning the rice husks etc. at the temperature range of between 500° C. or more and 700° C. or less, while stirring the rice husks etc., by introducing at atmospheric gas having a mass of 6.7 times or more and 20 times or less of the weight of the rice husks etc., oxygen gas having a weight of 1.4 times or more and 4 times or less with respect to the weight of the rice husks etc., or mixed gas of the atmospheric gas and the oxygen gas into the furnace, at the same time as burning, combustion gas generated at the time of combustion rice husks etc. is discharged from the furnace.

If the temperature of burning rice husks etc. is less than 500° C., there is a problem that benzopyrene which is a carcinogen is generated, and when the temperature of burning rice husks etc. exceeds 700° C., there is a problem that amorphous silica crystallizes and has carcinogenicity to the human body. In addition, when the atmospheric gas introduced into the furnace is less than 6.7 times the weight of rice husks etc., combustion of the rice husks etc. becomes incomplete, and the atmospheric gas introduced into the furnace exceeds 20 times the weight of the rice husks etc., the temperature in the furnace lowers and it becomes difficult to maintain the temperature. In addition, when the amount of oxygen introduced into the furnace is less than 1.4 times the weight of the rice husks etc., incomplete combustion of the rice husks etc. is caused and the oxygen introduced into the exceeds 4 times weight of the rice husks etc., there is a problem that the combustion of rice husks etc. is performed abruptly and the quality deteriorates as a combustion matter.

The present invention according to another embodiment is, a method of manufacturing an amorphous silica which is porous and easily soluble in water and which does not contain tar, crystal, residual agrichemicals and carcinogens, which comprising,
burning the rice husks etc. at the temperature range of between 550° C. or more and 650° C. or less, while stirring the rice husks etc.,
by introducing at atmospheric gas having a mass of 6.7 times or more and 20 times or less of the weight of the rice husks etc., oxygen gas having a weight of 1.4 times or more and 4 times or less with respect to the weight of the rice husks etc., or mixed gas of the atmospheric gas and the oxygen gas into the furnace,
at the same time as burning, combustion gas generated at the time of combustion rice husks etc. is discharged from the furnace.

When the temperature of burning the rice husks etc. is less than 550° C., there is a problem that it takes too much time for combustion. When the temperature of burning exceeds 650° C., amorphous silica in the rice husks etc. begins to be structured, and there is a problem that water solubility becomes difficult. In addition, atmospheric gas to be introduced into the furnace is less than 6.7 times the weight of rice husks etc., burning of the rice husks etc. becomes introduced incomplete, and the atmospheric gas to be introduced into the furnace exceeds 20 times the weight of rice husks etc., there is a problem that the furnace temperature decreases and it becomes difficult to maintain the temperature.

In addition, the oxygen introduced into the furnace exceeds 1.4 times the weight of rice husks etc., burning of the rice husks etc. becomes incomplete, and the oxygen introduced into the furnace exceeds 4 times the weight of rice husks etc. there is a problem that the combustion of rice husks etc. is performed abruptly and the quality deteriorates as a combustion matter.

The invention according to yet another embodiment is a combustion apparatus for obtaining combustion products by burning a rice husks etc. provided with a rotary kiln with a outside heater or rotary furnace with a screw,
the rotating shaft portion of the screw having a hollow portion and the atmosphere air being introduced into the hollow portion, and
having an exhaust mechanism for discharging the dry distillation gas generated during combustion of the rice husks etc. to the outside of the furnace.

The invention according to yet another embodiment is amorphous silica manufactured by the manufacturing method of the invention, wherein the amorphous silica is free of tar, crystal and carcinogens, is porous and water-soluble.

The invention according to yet another embodiment is a food containing amorphous silica produced by the method for producing amorphous silica according to the invention.

The invention according to yet another embodiment is a pharmaceutical product containing amorphous silica produced by the method for producing amorphous silica according to the invention.

The invention according to yet another embodiment is a cosmetic product containing amorphous silica produced by the method for producing amorphous silica according to the invention.

The invention according to yet another embodiment is a feed containing amorphous silica produced by the method for producing amorphous silica according to the invention.

Effect of the Invention

According to the process for producing amorphous silica according to the invention, the temperature range (500° C. to 700° C.) is set, and it is a possible to produce amorphous silica free from tar, crystal, residual agrichemicals and carcinogens, porous, and easy to be solved in water.

According to the method for producing amorphous silica according to the invention, an amorphous silica which is easily water-soluble, free of tar, crystal and carcinogens can be produced by setting an optimum temperature range (550° C. to 650° C.).

According to the method for producing amorphous silica according to the invention, amorphous silica can be produced stably by discharging the dry distillation gas containing tar generated from the raw material at the time of combustion to the outside of the furnace appropriately while setting above preferable temperature range.

The amorphous silica according to the invention is amorphous silica which is porous and easily soluble in water and does not contain tar, crystal, and carcinogens, and can be used for foods and the like.

According to the food according to the invention, it is possible to provide a food having effects such as reinforcement of human bones, skin beautification, reinforcement of nutritional components of blood vessels, enhancement of antioxidant power, and the like.

According to the medicine according to the invention, it is possible to provide a medicine having the effect of strengthening human bones, beautifying skin, reinforcing nutritional components of blood vessels, strengthening antioxidant power and the like.

The cosmetic product according to the invention can provide a cosmetic product having effects such as skin beautification, reinforcement of nutritional components of blood vessels and the like.

According to the feed according to the invention, it is possible to provide a feed effective for prevention of health and illness of livestock and cancer-producing animals and promotion of growth of chickens.

According to the present invention, porous and easy water soluble amorphous silica, method and apparatus to produce thereof can be obtained which does not contain tar, crystal, residual agrichemicals, and carcinogens by using only one burning treatment from a plant including silica abundantly such as rice plant like as rice husks constituting rice, rice straw, rice bran, wheat, corn, grass and horsetailes, tea, potato and the like.

EXPLANATION OF NUMBERS 1 indirect heating device
2 kilns
2a drying section
2b combustion part
2c internal space
2in entrance
2out exit
3 combustion chamber
3a exhaust pipe 4 heating source
5 piping section
6 cooling section
7 deodorizing part
8 dry distillation gas recovery section
9 auxiliary heating source
10 steam smoke route
11 lubricating section
12 water distribution pipe
13 fans
14 hopper
15 material supply piping
16 supply screw
17 second discharge pipe
18 cooling device
19 connection pipe (downstream exhaust pipe)
20 transport screw
21 transport screw
22 steam vent pipe (upstream exhaust gas pipe)
23 chimney section
24 circulating pipe
25 degassing pipe
26 atmosphere-oxygen supply pipe
30 connection
60 recovery section
31 helical blade
41 stirring blade
51 screw shaft
61 air supply opening
71 atmospheric supply pipe
81 oxygen supply tube
91 smoke eliminating device
P input material
Q material containing amorphous silica
100,101 charcoal of rice husks
200 capsules
300 capsule containers
400 capsules
500 capsule type food
501 pellet type food
600 binder

DETAILED DESCRIPTION OF THE INVENTION

The mode for carrying out the present invention is, a method of manufacturing an amorphous silica which is porous and easily soluble in water and which does not contain tar, crystal, residual agrichemicals and carcinogens, which comprising,
burning the rice husks etc. at the temperature range of between 500° C. or more and 700° C. or less, while stirring the rice husks etc.,
by introducing at atmospheric gas having a mass of 6.7 times or more and 20 times or less of the weight of the rice husks etc., oxygen gas having a weight of 1.4 times or more and 4 times or less with respect to the weight of the rice husks etc., or mixed gas of the atmospheric gas and the oxygen gas into the furnace,
at the same time as burning, combustion gas generated at the time of combustion rice husks etc. is discharged from the furnace.

The mode for carrying out the present invention is, a method of manufacturing an amorphous silica which is porous and easily soluble in water and which does not contain tar, crystal, residual agrichemicals and carcinogens, which comprising,
burning the rice husks etc. at the temperature range of between 550° C. or more and 650° C. or less, while stirring the rice husks etc., by introducing at atmospheric gas having a mass of 6.7 times or more and 20 times or less of the weight of the rice husks etc., oxygen gas having a weight of 1.4 times or more and 4 times or less with respect to the weight of the rice husks etc., or mixed gas of the atmospheric gas and the oxygen gas into the furnace,
at the same time as burning, combustion gas generated at the time of combustion rice husks etc. is discharged from the furnace.

Here, amorphous silica which is a combustion product such as rice husks or the like is readily soluble in water even at a temperature within the range of 40° C. or less in the living body temperature.

A combustion device according to an embodiment of the present invention is a combustion device that burns rice husks or the like to obtain a combustion product such as rice husks, wherein the combustion device is configured to rotate a rotary kiln or a screw Wherein a rotating shaft portion of the screw has a hollow portion, atmosphere or oxygen or a mixture thereof is introduced into the hollow portion, and exhaust gas generated upon combustion of the rice husks or the like is supplied to a furnace And has an exhaust mechanism for discharging the exhaust gas to the outside.

EXAMPLE

Example 1

Figure 1:
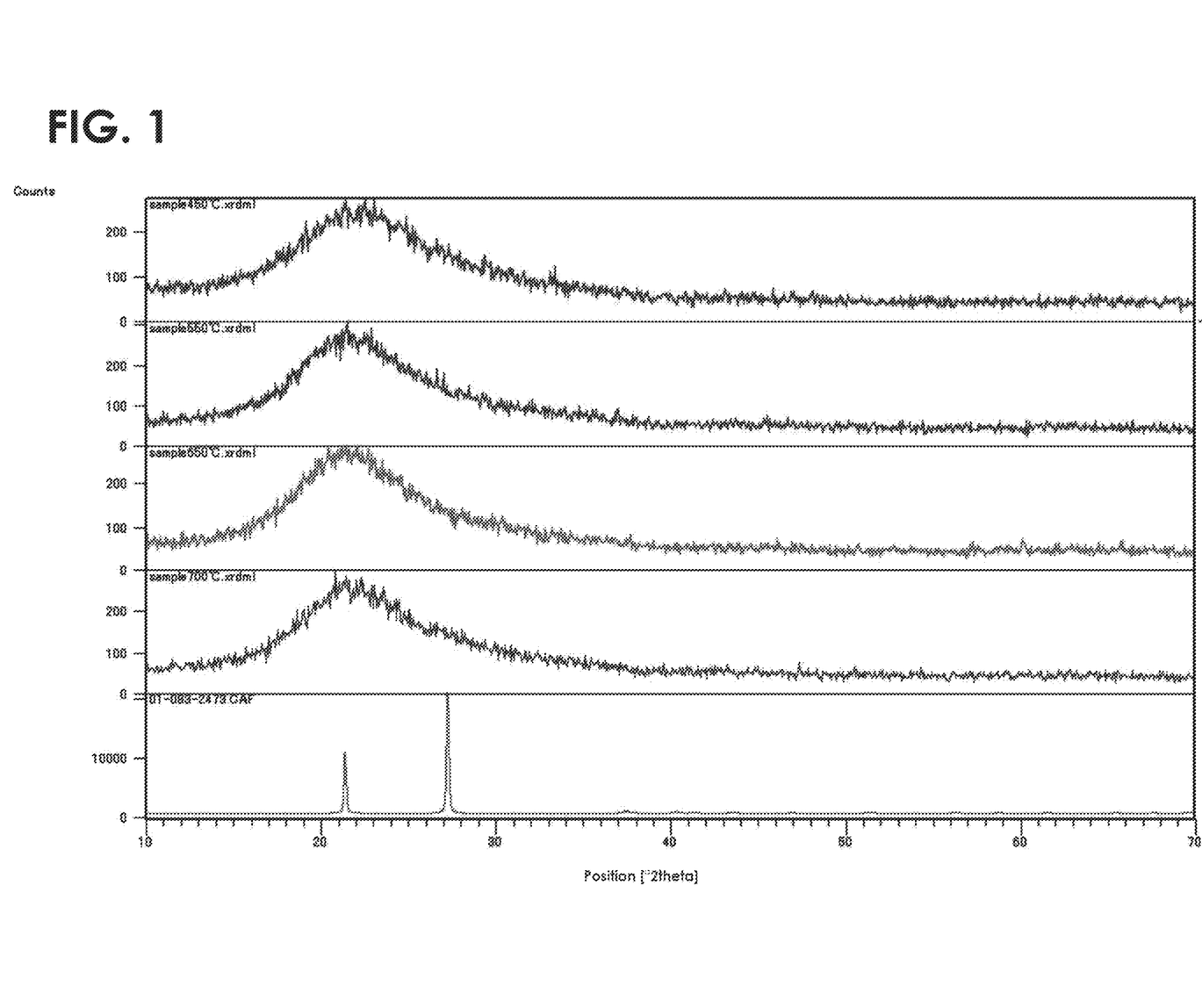
FIG. 1 is a diagram of an X-ray analytical spectrum of a combustion product of rice husks.

FIG. 1 is a diagram of an X-ray analytical spectrum of a combustion product of rice husks.

An X-ray analytical spectrum diagram in the case of combustion temperature 450° C., combustion temperature 550° C., combustion temperature 650° C., combustion temperature 700° C. are shown in order from upward in FIG. In either case, it is found that the shape of the X-ray analysis spectrum is a broad shape without a peak showing crystallinity, and the rice husks combustion product is amorphous.

Example 2

Figure 2:
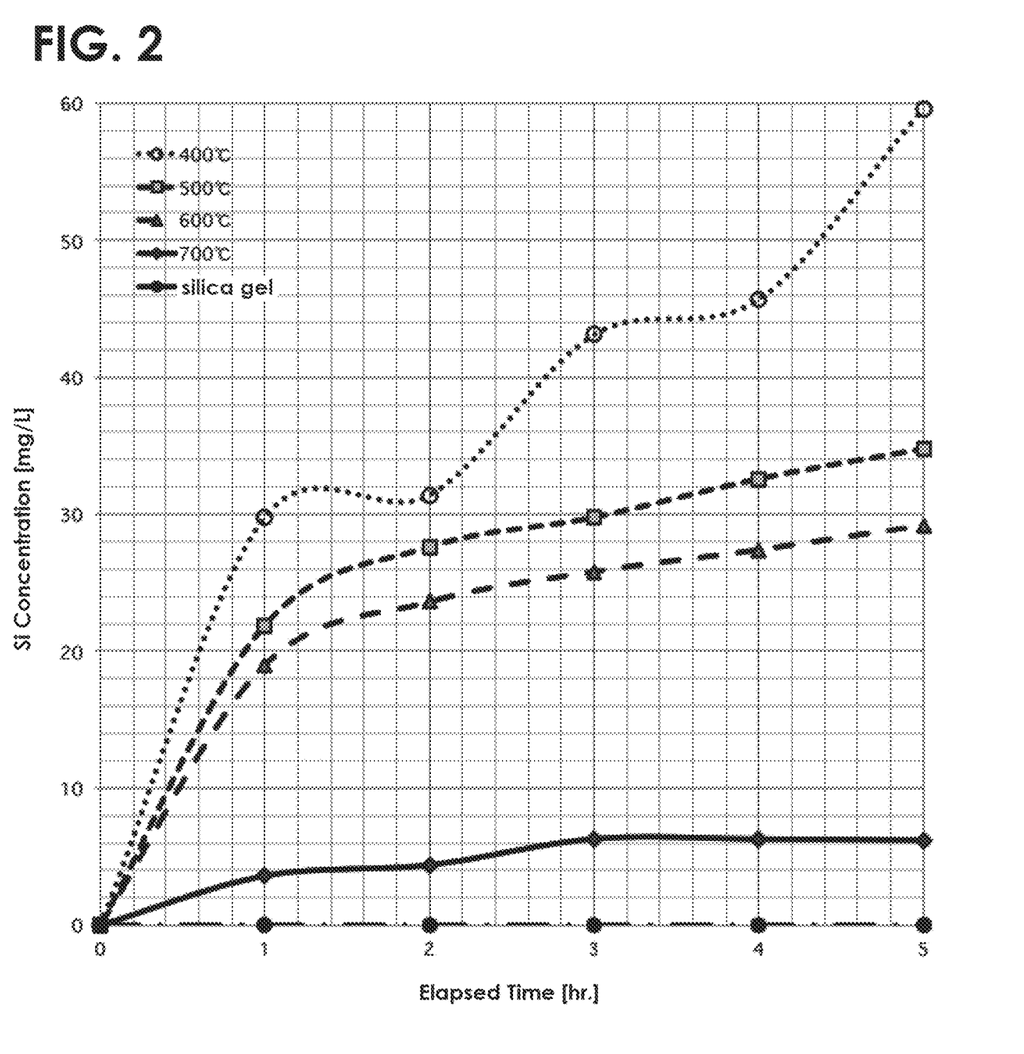
FIG. 2 is soluble test results of the combustion product of the rice husks in purified water at 40° C.

FIG. 2 shows the dissolution test results of the combustion product of the rice husks in purified water at 40° C.

From the test results shown in FIG. 2, it can be seen that the lower the production temperature, the better the water solubility. Also, in the case of "silica gel" which is one type of amorphous silica, it is found that it is hardly dissolved. Considering the results of the X-ray analysis shown in FIGS. 1 and 2, even if it is amorphous silica, not all of them are easily water-solubilized but their properties are greatly different depending on the production temperature and the manufacturing method. Although the manufacturing temperature is low, rice husk burned materials have high water solubility, but the production time is long and economic efficiency is not excellent. Also, if it is below 500° C., it is likely to produce benzotriazole which is a carcinogenic substance, so it is not suitable for edible use. When the production temperature is high, the production becomes easy, but the water solubility becomes low. It is generally considered that the combustion product of the rice husks exceeding 800° C. will crystallize, and crystalline silica is also considered to be carcinogenic, so it is also not suitable for edible use.

Therefore, amorphous silica which does not contain carcinogens and has high water solubility means that the temperature is as low as possible at a production temperature of 500° C. or higher. Considering the production efficiency for this, the optimum production temperature for practical use is in the range of 550 to 650° C.

Example 3

Various analyzes were carried out on amorphous silica obtained from rice husk burned material at a combustion temperature of 600° C. A series of results will be described. The inspection agency is Japan Food Function Analysis Research Institute Co., Ltd.

Table 1 shows the test results on the bacteria of the amorphous silica-containing rice husk burned material of the present invention.

From Table 1, it is found that the number of general viable bacteria is 300 or less/g, and the coliform bacteria group is negative.

TABLE 1

Test Results about Bacteria of Rice Hull Burned Material containing Amorphous Silicon

| Test Items | Test Result | Detection Limit | Test Method |
|---|---|---|---|
| number of general viable bacteria | 300 or less/g | — | standard agar plate culture method |
| coliform bacteria group (qualitative analysis) | negative | — | BGLB medium culture method |

Table 2 is an analysis on the content of amorphous silica of the present invention. 41000 mg of silica was confirmed in the rice husk burned material in 100 g.

TABLE 2

Content of Amorphous Silicon

| Test Item | Test Result | Detection Limit | Test Method |
|---|---|---|---|
| silicon | 41000 mg/100 g | — | absorption photometry |

Table 3 shows the test results concerning the presence or absence of the amorphous silica radioactive substance of the present invention.

From Table 3, radioactive iodine and radioactive cesium are not detected.

TABLE 3

Presence/Absence of Amorphous Silicone Radioactive Substance

| Test Items | Test Result | Detection Limit |
|---|---|---|
| radioactive iodine (iodine-131) | not detected | 3.6 Bq/kg |
| radioactive cesium | not detected | — |
| sesium-134 | not detected | 5.0 Bq/kg |
| sesium-137 | not detected | 4.0 Bq/kg |

Table 4 shows the test results of the presence or absence of harmful metals and the presence or absence of carcinogens of the amorphous silica-containing burned rice flour.

From Table 4, it was found that the carcinogenic substance, benzpyrene, was not detected.

TABLE 4

Presence/Absence of Harmful Metals and Carcinogenic Substances of Rice Hull Burned Material including Amorphous Silicone

| Test Items | Test Result | Detection Limit | Test Mothod |
|---|---|---|---|
| cadmium | 0.02 ppm | — | ICP emission spectroscopy |
| lead | 0.2 ppm | — | ICP emission spectroscopy |
| arsenicum | not detected | 0.1 ppm | ICP emission spectroscopy |
| mercury | not detected | 0.01 ppm | gold amalgam method |
| benzpyrene | not detected | 0.01 ppm | gas chromatograph mass spectroscopy |

Table 5 shows the test results of the detection of residual agrichemicals of amorphous silica-containing rice husk burned materials of the present invention.

Residual pesticides (276 items) were all undetected.

Tables 6, 7, 8, and 9 show a list of concrete residual agrichemical items.

TABLE 5

Detection of Residual Agrichemicals in Rice Hull Burned Material Including Amorphous Silicon

| Test Items | Test Result | Detection Limit | Test Method |
|---|---|---|---|
| residual agrichemicals | all undetected | 0.1 ppm | simultenaous analysis with 276 items |

TABLE 6

List of Residual Agrichemicals (1)

| Analysis Items | Result of Analysis | Detection Limit | Analytical Method |
|---|---|---|---|
| BHC (summation of α β γ and δ) | not detected | 0.1 | *1 |
| BHC (α) | not detected | 0.1 | *1 |
| BHC (β) | not detected | 0.1 | *1 |
| BHC (γ) | not detected | 0.1 | *1 |
| BHC (δ) | not detected | 0.1 | *1 |
| EPN | not detected | 0.1 | *1 |
| IBP | not detected | 0.1 | *1 |
| op'-OOD | not detected | 0.1 | *1 |
| op'-OOE | not detected | 0.1 | *1 |
| op'-OOT | not detected | 0.1 | *2 |
| pp'-OOD | not detected | 0.1 | *1 |
| pp'-OOE | not detected | 0.1 | *1 |
| pp'-OOT | not detected | 0.1 | *1 |
| XMO | not detected | 0.1 | *1 |
| acrinathrin | not detected | 0.1 | *1 |
| azaconazole | not detected | 0.1 | *1 |
| azinphos-methyl | not detected | 0.1 | *1 |
| acetamiprid | not detected | 0.1 | *2 |
| acetochlor | not detected | 0.1 | *1 |
| azoxystrobin | not detected | 0.1 | *2 |
| atrazine | not detected | 0.1 | *1 |
| anilofos | not detected | 0.1 | *1 |
| amitraz | not detected | 0.1 | *1 |
| ametrine | not detected | 0.1 | *1 |
| alachlor | not detected | 0.1 | *1 |
| aldrin | not detected | 0.1 | *1 |
| allethrin | not detected | 0.1 | *1 |
| isouron | not detected | 0.1 | *2 |
| isoxathion | not detected | 0.1 | *2 |
| isofenphos | not detected | 0.1 | *1 |
| isofenphos oxon | not detected | 0.1 | *1 |

TABLE 6-continued

List of Residual Agrichemicals (1)

| Analysis Items | Result of Analysis | Detection Limit | Analytical Method |
|---|---|---|---|
| isoprocarb | not detected | 0.1 | *1 |
| isoprothiolane | not detected | 0.1 | *1 |
| iprobenfos | not detected | 0.1 | *1 |
| imazosulfuron | not detected | 0.1 | *2 |
| imidacloprid | not detected | 0.1 | *2 |
| indoxacarb | not detected | 0.1 | *2 |
| uniconazole P | not detected | 0.1 | *1 |
| esprocarb | not detected | 0.1 | *1 |
| ethalfluralin | not detected | 0.1 | *1 |
| ethion | not detected | 0.1 | *1 |
| ethylchiometon | not detected | 0.1 | *1 |
| edifenphos | not detected | 0.1 | *1 |
| etoxazole | not detected | 0.1 | *1 |
| etofenprox | not detected | 0.1 | *1 |
| ethoprophos | not detected | 0.1 | *1 |
| α-endosulfan | not detected | 0.1 | *1 |
| β-endosulfan | not detected | 0.1 | *1 |
| endrin | not detected | 0.1 | *1 |
| oxadiazon | not detected | 0.1 | *1 |
| oxadixyl | not detected | 0.1 | *1 |
| oxaziclomefone | not detected | 0.1 | *1 |
| oxyfluorfen | not detected | 0.1 | *1 |
| orysastrobin | not detected | 0.1 | *1 |
| cadusafos | not detected | 0.1 | *1 |
| cafenstrole | not detected | 0.1 | *2 |
| calbaryl (NAC) | not detected | 0.1 | *1 |
| karbutilate | not detected | 0.1 | *2 |
| carbendazole (MBC) | not detected | 0.1 | *2 |
| carbofuran | not detected | 0.1 | *1 |
| quinalphos | not detected | 0.1 | *1 |
| quinoxyfen | not detected | 0.1 | *1 |
| quinoclamine | not detected | 0.1 | *1 |
| captan | not detected | 0.1 | *1 |
| quintozene | not detected | 0.1 | *1 |
| kresoxim-methyl | not detected | 0.1 | *1 |
| clothianidin | not detected | 0.1 | *2 |
| chromafenozide | not detected | 0.1 | *2 |
| chlorthal-dimethyl | not detected | 0.1 | *1 |
| chlorothalonil (TPN) | not detected | 0.1 | *1 |
| chlordane (cis) | not detected | 0.1 | *1 |
| chlordane (trans) | not detected | 0.1 | *1 |
| chlorpyrifos | not detected | 0.1 | *1 |
| chlorpyrifos-methyl | not detected | 0.1 | *1 |
| chlorfenapyr | not detected | 0.1 | *1 |

Analytical Method:
*1 Gas Chromatograph Mass Spectrometry,
*2 Liquid Chromatograph Mass Spectrometry

TABLE 7

List of Residual Agrichemicals (2)

| Analysis Items | Result of Analysis | Detection Limit | Analytical Method |
|---|---|---|---|
| chlorfenvinphos (E) | not detected | 0.1 | *1 |
| chlorfenvinphos (Z) | not detected | 0.1 | *1 |
| chlorpropham | not detected | 0.1 | *1 |
| chlorobenzilate | not detected | 0.1 | *1 |
| cyanazine | not detected | 0.1 | *1 |
| cyanophos | not detected | 0.1 | *1 |
| diuron (DCMU) | not detected | 0.1 | *2 |
| diethofencarb | not detected | 0.1 | *1 |
| diclocymet - 1 | not detected | 0.1 | *1 |
| diclocymet - 2 | not detected | 0.1 | *1 |
| dichlofenthion | not detected | 0.1 | *1 |
| dichlobenil (DBN) | not detected | 0.1 | *1 |
| diclofop-methyl | not detected | 0.1 | *1 |
| dicloran | not detected | 0.1 | *1 |
| dichlorvos (DDVP) | not detected | 0.1 | *2 |
| cyhalothrin | not detected | 0.1 | *1 |
| cyhalohop butyl | not detected | 0.1 | *1 |
| diphenamid | not detected | 0.1 | *1 |
| difenoconazole | not detected | 0.1 | *1 |
| cyfluthrin - 1 | not detected | 0.1 | *1 |
| cyfluthrin - 2 | not detected | 0.1 | *1 |
| cyfluthrin - 3 | not detected | 0.1 | *1 |
| diflufenican | not detected | 0.1 | *1 |
| cyproconazole | not detected | 0.1 | *1 |
| cyprodinil | not detected | 0.1 | *1 |
| cypermethrin - 1 | not detected | 0.1 | *1 |
| cypermethrin - 2 | not detected | 0.1 | *1 |
| cypermethrin - 3 | not detected | 0.1 | *1 |
| cypermethrin - 4 | not detected | 0.1 | *1 |
| simazine | not detected | 0.1 | *1 |
| dimethametryn | not detected | 0.1 | *1 |
| dimethylvinphos (Z) | not detected | 0.1 | *1 |
| dimethenanid | not detected | 0.1 | *1 |
| dimethoate | not detected | 0.1 | *1 |
| simetryn | not detected | 0.1 | *1 |
| dimepiperate | not detected | 0.1 | *1 |
| silafluofen | not detected | 0.1 | *1 |
| spinosyn A | not detected | 0.1 | *2 |
| spinosyn D | not detected | 0.1 | *2 |
| spiroxamine - 1 | not detected | 0.1 | *1 |
| spiroxamine - 2 | not detected | 0.1 | *1 |
| zoxamide | not detected | 0.1 | *1 |
| terbacil | not detected | 0.1 | *1 |
| diazinon | not detected | 0.1 | *1 |
| daimuron | not detected | 0.1 | *2 |
| thiacloprid | not detected | 0.1 | *2 |
| thiamethoxam | not detected | 0.1 | *2 |
| thiophanate-methyl | not detected | 0.1 | *2 |
| thiobencarb | not detected | 0.1 | *1 |
| thifensulfuron-methyl | not detected | 0.1 | *2 |
| thifluzamide | not detected | 0.1 | *1 |
| dieldrin | not detected | 0.1 | *1 |
| tecnazene | not detected | 0.1 | *1 |
| tetrachlorvinphos | not detected | 0.1 | *1 |
| tetraconazole | not detected | 0.1 | *1 |
| tetradiphon | not detected | 0.1 | *1 |
| thenylchlor | not detected | 0.1 | *1 |
| tebuconazole | not detected | 0.1 | *1 |
| tebufenozide | not detected | 0.1 | *2 |
| tebufenpyrad | not detected | 0.1 | *1 |
| tefluthrin | not detected | 0.1 | *1 |
| deltamethrin | not detected | 0.1 | *1 |
| terbutryn | not detected | 0.1 | *1 |
| terbufos | not detected | 0.1 | *1 |
| tralomethrin | not detected | 0.1 | *1 |
| triadimenol | not detected | 0.1 | *1 |
| triadimefon | not detected | 0.1 | *1 |
| triazophos | not detected | 0.1 | *1 |
| tri-allate | not detected | 0.1 | *1 |
| tricyclazole | not detected | 0.1 | *2 |
| tribuphos | not detected | 0.1 | *1 |
| triflumizole | not detected | 0.1 | *2 |
| triflumizole metabolite | not detected | 0.1 | *2 |
| trifluralin | not detected | 0.1 | *1 |
| trifloxystrobin | not detected | 0.1 | *1 |

Analytical Method:
*1 Gas Chromatograph Mass Spectrometry,
*2 Liquid Chromatograph Mass Spectrometry

TABLE 8

List of Residual Agrichemicals (3)

| Analysis Items | Result of Analysis | Detection Limit | Analytical Method |
|---|---|---|---|
| tolclofos-methyl | not detected | 0.1 | *1 |
| tolfenpyrad | not detected | 0.1 | *1 |
| napropamide | not detected | 0.1 | *1 |

TABLE 8-continued

List of Residual Agrichemicals (3)

| Analysis Items | Result of Analysis | Detection Limit | Analytical Method |
|---|---|---|---|
| nitrothal-isopropyl | not detected | 0.1 | *1 |
| norflurazon | not detected | 0.1 | *1 |
| paclobutrazol | not detected | 0.1 | *1 |
| parathion | not detected | 0.1 | *1 |
| parathion-methyl (methyl-parathion) | not detected | 0.1 | *1 |
| halfenprox | not detected | 0.1 | *1 |
| bitertanol | not detected | 0.1 | *1 |
| bifenox - 1 | not detected | 0.1 | *1 |
| bifenox - 2 | not detected | 0.1 | *1 |
| bifenthrin | not detected | 0.1 | *1 |
| piperophos | not detected | 0.1 | *1 |
| pyraclofos | not detected | 0.1 | *1 |
| pyrazosulfuron-ethyl | not detected | 0.1 | *2 |
| pyrazophos | not detected | 0.1 | *1 |
| pyrazolate | not detected | 0.1 | *2 |
| pyraflufen-ethyl | not detected | 0.1 | *1 |
| pyridafenthion | not detected | 0.1 | *1 |
| pyridaben | not detected | 0.1 | *1 |
| pyrifenox (E) | not detected | 0.1 | *1 |
| pyrifenox (Z) | not detected | 0.1 | *1 |
| pyriftalid | not detected | 0.1 | *2 |
| pyributicarb | not detected | 0.1 | *1 |
| pyriproxyfen | not detected | 0.1 | *1 |
| pyriminobac-methyl (E) | not detected | 0.1 | *1 |
| pyriminobac-methyl (Z) | not detected | 0.1 | *1 |
| pirimiphos-methyl | not detected | 0.1 | *1 |
| pyrimethanil | not detected | 0.1 | *1 |
| pyrethin - 1 | not detected | 0.1 | *1 |
| pyrethin - 2 | not detected | 0.1 | *1 |
| pyroquilon | not detected | 0.1 | *2 |
| vinclozolin | not detected | 0.1 | *1 |
| fipronil | not detected | 0.1 | *1 |
| fenamiphos | not detected | 0.1 | *1 |
| fenarimol | not detected | 0.1 | *1 |
| fenitrothion | not detected | 0.1 | *1 |
| fenoxanil | not detected | 0.1 | *1 |
| fenothiocarb | not detected | 0.1 | *1 |
| phenothrin - 1 | not detected | 0.1 | *1 |
| phenothrin - 2 | not detected | 0.1 | *1 |
| fenobucarb | not detected | 0.1 | *1 |
| ferimzone (Z) | not detected | 0.1 | *1 |
| fensulfothion | not detected | 0.1 | *1 |
| fenthion | not detected | 0.1 | *1 |
| phenthoate | not detected | 0.1 | *1 |
| fentrazamide | not detected | 0.1 | *2 |
| fenvalerate - 1 | not detected | 0.1 | *1 |
| fenvalerate - 2 | not detected | 0.1 | *1 |
| fenpyroximate | not detected | 0.1 | *2 |
| fenbuconazole | not detected | 0.1 | *1 |
| fenpropathrin | not detected | 0.1 | *1 |
| fenpropimorph | not detected | 0.1 | *1 |
| fthalide | not detected | 0.1 | *1 |
| butachlor | not detected | 0.1 | *1 |
| butamifos | not detected | 0.1 | *1 |
| bupirimate | not detected | 0.1 | *1 |
| buprofezin | not detected | 0.1 | *1 |
| flazasulfuron | not detected | 0.1 | *2 |
| flamprop-methyl | not detected | 0.1 | *1 |
| fluacrypyrim | not detected | 0.1 | *1 |
| fluquinconazole | not detected | 0.1 | *1 |
| flucythrinate - 1 | not detected | 0.1 | *1 |
| flucythrinate - 2 | not detected | 0.1 | *1 |
| flutolanil | not detected | 0.1 | *1 |
| fluvalinate | not detected | 0.1 | *2 |
| flufenoxuron | not detected | 0.1 | *2 |
| flubendiamide | not detected | 0.1 | *2 |
| flumioxazin | not detected | 0.1 | *1 |
| flumiclorac-pentyl | not detected | 0.1 | *1 |
| fluridone | not detected | 0.1 | *1 |
| pretilachlor | not detected | 0.1 | *1 |
| prodiamine | not detected | 0.1 | *1 |
| procymidone | not detected | 0.1 | *1 |

Analytical Method:
*1 Gas Chromatograph Mass Spectrometry,
*2 Liquid Chromatograph Mass Spectrometry

TABLE 9

List of Residual Agrichemicals (4)

| Analysis Items | Result of Analysis | Detection Limit | Analytical Method |
|---|---|---|---|
| prothiofos | not detected | 0.1 | *1 |
| propachlor | not detected | 0.1 | *1 |
| propazine | not detected | 0.1 | *1 |
| propanil | not detected | 0.1 | *1 |
| propargite | not detected | 0.1 | *1 |
| propiconazole - 1 | not detected | 0.1 | *1 |
| propiconazole - 2 | not detected | 0.1 | *1 |
| propyzamide | not detected | 0.1 | *1 |
| prohydrojasmon - 1 | not detected | 0.1 | *1 |
| prohydrojasmon - 2 | not detected | 0.1 | *1 |
| profenofos | not detected | 0.1 | *1 |
| propoxur | not detected | 0.1 | *1 |
| bromacil | not detected | 0.1 | *1 |
| prometryn | not detected | 0.1 | *1 |
| bromobutide | not detected | 0.1 | *1 |
| bromopropylate | not detected | 0.1 | *1 |
| bromophos | not detected | 0.1 | *1 |
| hexaconazole | not detected | 0.1 | *1 |
| hexazinone | not detected | 0.1 | *1 |
| benalaxyl | not detected | 0.1 | *1 |
| benoxacor | not detected | 0.1 | *1 |
| permethrin (isomer 1) | not detected | 0.1 | *1 |
| permethrin (isomer 2) | not detected | 0.1 | *1 |
| penconazole | not detected | 0.1 | *1 |
| pencycuron | not detected | 0.1 | *1 |
| bensulfuron-methyl | not detected | 0.1 | *2 |
| benzobicyclon | not detected | 0.1 | *2 |
| pendimethalin | not detected | 0.1 | *1 |
| benfuracarb | not detected | 0.1 | *1 |
| benfluralin | not detected | 0.1 | *1 |
| benfuresate | not detected | 0.1 | *1 |
| phosalone | not detected | 0.1 | *1 |
| boscalid | not detected | 0.1 | *1 |
| fosthiazate | not detected | 0.1 | *1 |
| phosphamidon | not detected | 0.1 | *1 |
| phosmet | not detected | 0.1 | *1 |
| malachion | not detected | 0.1 | *1 |
| myclobutanil | not detected | 0.1 | *1 |
| methidathion | not detected | 0.1 | *1 |
| methoxychlor | not detected | 0.1 | *1 |
| metominostrobin | not detected | 0.1 | *2 |
| metolachlor | not detected | 0.1 | *1 |
| metribuzin | not detected | 0.1 | *2 |
| mepanipyrim | not detected | 0.1 | *1 |
| mevinphos | not detected | 0.1 | *1 |
| mefenacet | not detected | 0.1 | *1 |
| mefenoxam | not detected | 0.1 | *1 |
| mefenpyr-diethyl | not detected | 0.1 | *1 |
| mepronil | not detected | 0.1 | *1 |
| monocrotophos | not detected | 0.1 | *1 |
| linuron | not detected | 0.1 | *2 |
| lenacil | not detected | 0.1 | *1 |

Analytical Method:
*1 Gas Chromatograph Mass Spectrometry,
*2 Liquid Chromatograph Mass Spectrometry Using the amorphous silica-containing rice husk burned material of the present invention as a specimen, in accordance with the OECD Guideline for the Testing of Chemicals 404 (2002), a skin primary irritation test using a rabbit was performed.

The specimens were closed to the intact and scarred skin of 3 rabbits for 24 hours. As a result, 1 hour after removal, very mild to clear erythema was seen in all cases, and in 2 cases very mild edema was seen but disappeared by 72 hours.

ISO 10993-10 Biological
Evaluation of Medical
The primary irritation index (PII) obtained according to Devices—Part 10 (2010) was 0.4.

From the above, in the primary skin irritation test using rabbits, specimens were evaluated as falling within the category of "nonirritating".

Acute oral toxicity test (limit test) using rats was conducted using the amorphous silica-containing burned rice flour sample as a specimen of the present invention. Samples at a dose of 2,000 mg/kg were orally administered to the test group to male and female rats as water control for solvent control as control group and observed for 14 days. As a result, no abnormalities and deaths were observed during the observation period. From the above, it was evaluated that in a single oral administration using rats, the LD50 value of the specimen exceeded 2,000 mg/kg in both males and females.

Example 4

Application to Food and Medicine

The amorphous silica of the present invention is effective for improving the bone density of the human body. Subjects From the age of 40 to the age of 80, the bone density tended to rise as a result of giving the amorphous silica of the present invention every day. Application as a supplement to improve bone density is also possible.

Table 10 shows that bone density before and after ingestion is measured by ingesting about 100 mg of amorphous silica containing powder of the present invention (silica content 40% or more) in 10 males and females age 45 to 82 years a day It is the result.

Here, Table 10 shows the ultrasonic bone density measurement result of the bone of the subject's heel.

TABLE 10

Measurement Results about Influence on Bone Density of Amorphous Silicon

| Age, Sex | Before Ingestion (m/s) | After Ingestion (m/s) | Ingestion Period (day) | Increase or Decrease (±m/s) |
| --- | --- | --- | --- | --- |
| 51 years old, Man | 1467.9 | 1473.6 | 193 | +5.7 |
| 58 years old, Man | 1443.6 | 1472.4 | 187 | +28.8 |
| 45 years old, Woman | 1514.7 | 1547.5 | 191 | +32.8 |
| 53 years old, Woman | 1482.1 | 1483.7 | 200 | +1.6 |
| 61 years old, Woman (1) | 1458.4 | 1481.3 | 187 | +22.9 |
| 61 years old, Woman (2) | 1456.9 | 1478.4 | 182 | +21.5 |
| 62 years old, Woman | 1509.7 | 1524.6 | 201 | +14.9 |
| 72 years old, Woman | 1451.2 | 1477.5 | 194 | +26.3 |
| 75 yaers old, Woman | 1443.6 | 1469.7 | 182 | +26.1 |
| 82 years old, Woman | 1467.3 | 1484.9 | 198 | +17.6 |

According to Table 10, it is understood that the bone densities of all subjects, men and women aged 45 to 82 years, increased before and after ingestion by all subjects.

Furthermore, silica is absorbed from the intestinal wall and has the effect of solubilizing adherents inside the defect as it passes through the blood vessel, which is effective also in preventing arteriosclerosis.

Example 5

Application to Cosmetics

Silica is also contained in the human body and exists in hair, nails, blood vessels, bones, joints and cell walls. In vivo silica has a function of bundling collagen, it helps regeneration, reinforcement and maintenance of bones, hair, nails, and collagen, as well as skin moisture retention and the like.

Example 6

Application to Feed

This example is an example in which amorphous silica of the present invention is mixed with feed. It is a method of mixing amorphous silica directly into livestock feed. This will promote the health of livestock and cancer-giving animals, and will also improve meat quality.

Example 7

Figure 3:
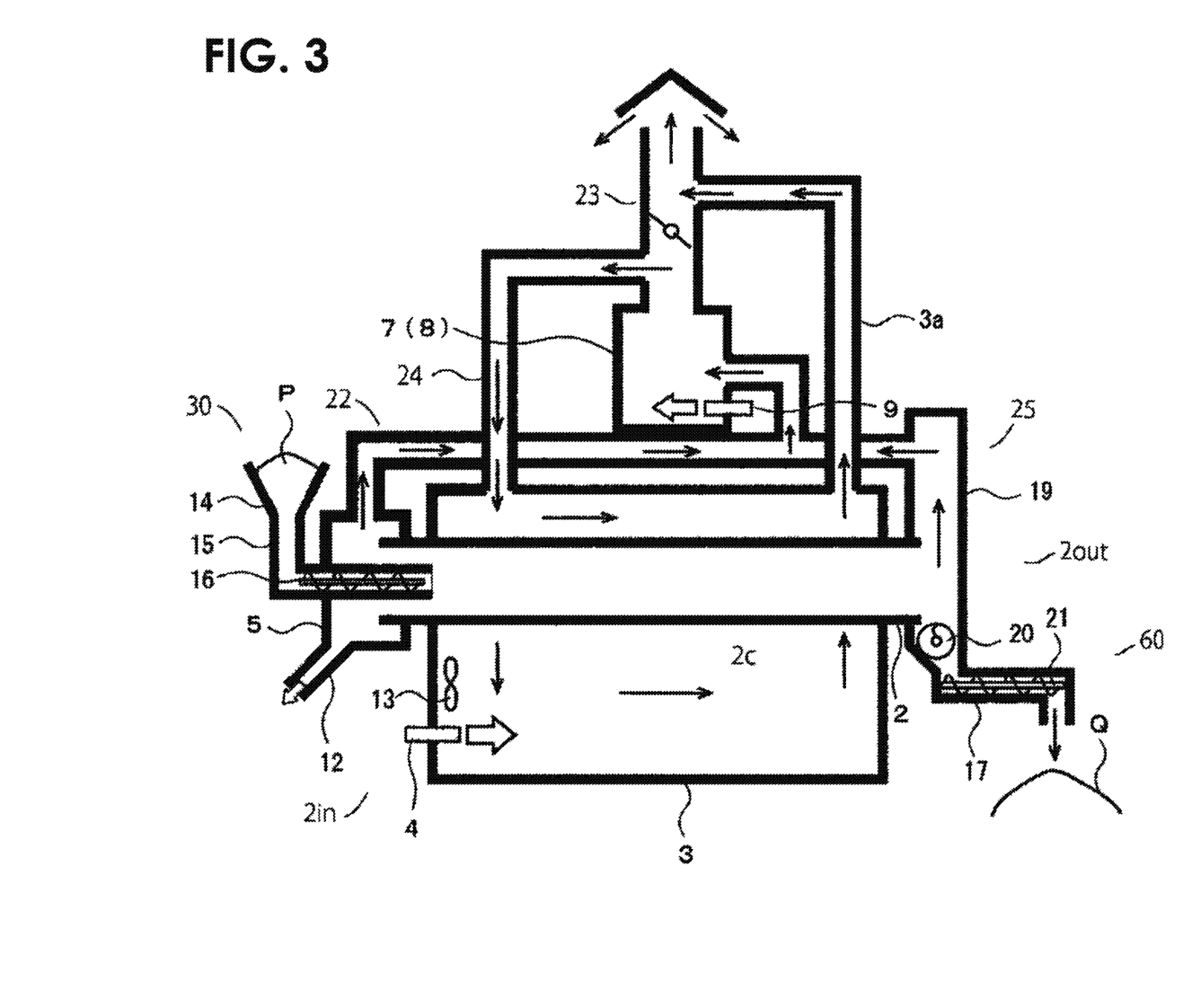
FIG. 3 is a view of a combustion apparatus according to this embodiment.

FIG. 3 is a diagram of the combustion apparatus of this embodiment.

The combustion apparatus used in the present invention has,
a rotating kiln 2 having helical blade and stirring blades disposed therein, an air/oxygen supply pipe 26 for supplying atmospheric air or oxygen or a mixed gas of said atmosphere and said oxygen,
a combustion chamber 3 for supplying heat to the entire interior of one kiln 2 by burning rice husks etc. while indirectly heating the rice husks or the like thrown into the one kiln 2,
a heating source 4 such as a burner facing the inside of the combustion chamber 3,
a drying section 2a which is set in the inside of the kiln 2 so as to evaporate moisture contained in the rice husks etc. thrown into the kiln 2 by indirect heating of the combustion chamber 3, and
a combustion section 2b which is set in the inside of the kiln 2 so as to burn rice husks etc. dried in the drying section 2a.

Example 8

Figure 4:
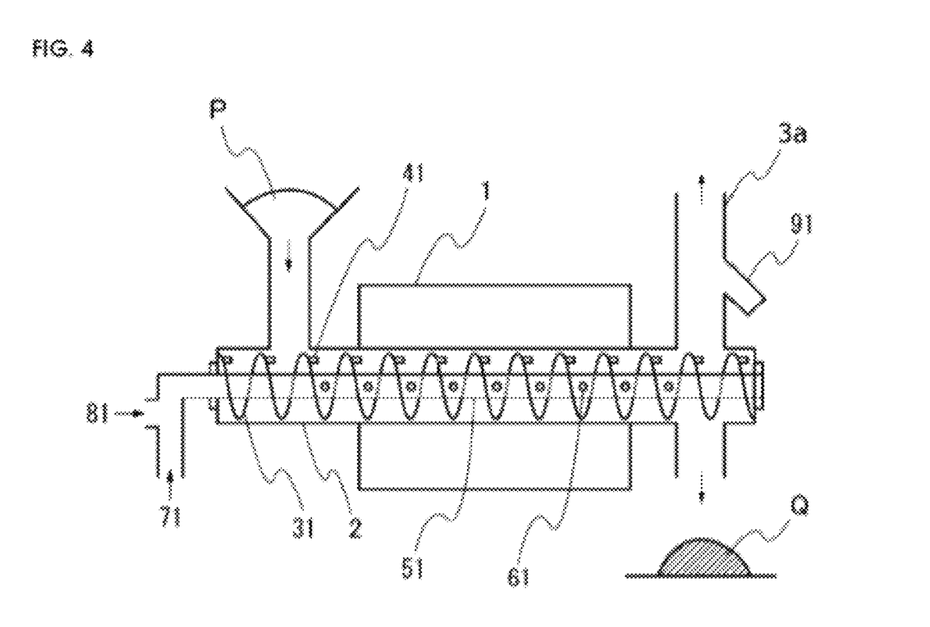
FIG. 4 is a view showing another example of the combustion device of the present embodiment.

FIG. 4 is a diagram of another example of the combustion device of this embodiment.

The combustion apparatus used in the present invention has
a pipe 71 for supplying atmospheric air,
a pipe 81 for supplying oxygen,
an indirect heating device 1 such as an electric furnace capable of setting an arbitrary temperature,
Kiln 2,
an opening portion 61 of a rotating screw shaft for supplying the atmospheric air, the oxygen or a mixed gas thereof into the kiln,
a helical blade 31, and
stirring blades 41.

INDUSTRIAL APPLICABILITY

According to the present invention, the combustion treatment is one step, rich in rice plant, rice straw, rice bran, rice family plants such as wheat, corn, grass, and the like, and horsetail, tea, potato, etc. Amorphous silicon that is used for foods, medicines, cosmetics, and feeds that do not contain tar, crystal, residual agrichemicals and carcinogens from vegetable silicon and are easily porous and soluble in water, and methods and apparatus for producing the same It contributes to the promotion of human health and the development of livestock industry.

The invention claimed is:

1. A method of manufacturing an amorphous silica by burning rice husks in a combustion apparatus, where the combustion apparatus includes a rotating kiln (2), a combustion chamber (3) for supplying heat to an entire interior of the kiln (2), and a heating source (4) facing the inside of the combustion chamber (3), the kiln (2) having a helical blade (31) and stirring blades (41) disposed therein, a material supply piping (15) having a supply screw (16) disposed upstream thereof, an upstream exhaust gas pipe (22) disposed upstream thereof, a downstream exhaust gas pipe (19) disposed downstream thereof, a water distribution pipe (12) at an end of the kiln (2), a drying section (2a) being set in the inside thereof to evaporate moisture contained in the rice husks, and a combustion section (2b) which is set in the inside thereof to burn the rice husks dried in the drying section (2a), and an atmosphere-oxygen supply pipe (26) for supplying atmosphere gas or oxygen gas into the inside of the kiln (2), the method comprising:

supplying the rice husks into the inside of the kiln (2) via the material supply piping (15) by the screw (16);

evaporating moisture contained in the rice husks by indirect heating of the combustion chamber (3);

burning the rice husks at a temperature range between 500° C. or more and 700° C. or less by introducing atmospheric gas having a mass of 6.7 times or more and 20 times or less of the weight of the rice husks, or oxygen gas having a weight of 1.4 times or more and 4 times or less with respect to the weight of the rice husks into the inside of the kiln (2) through the atmosphere-oxygen supply pipe (26) while stirring the rice husks; and at the same time as said burning, discharging combustion gas generated at the time of combustion of the rice husks from the upstream exhaust gas pipe (22) and the downstream exhaust gas pipe (19).

2. The method of manufacturing an amorphous silica according to claim 1, wherein the rice husks are burned at the temperature range of between 550° C. or more and 650° C. or less.

3. A combustion apparatus, comprising:

a rotating kiln (2);

a combustion chamber (3) for supplying heat to an entire interior of the kiln (2); and a heating source (4) facing the inside of the combustion chamber (3), the kiln (2) having a helical blade (31) and stirring blades (41) disposed therein, a material supply piping (15) having a supply screw (16) disposed upstream thereof, an upstream exhaust gas pipe (22) disposed upstream thereof, a downstream exhaust gas pipe (19) disposed downstream thereof, a water distribution pipe (12) at an end of the kiln (2), a drying section (2a) which is set in the inside thereof configured so as to evaporate moisture contained in the rice husks, a combustion section (2b) which is set in the inside thereof configured so as to burn the rice husks dried in the drying section (2a), and an atmosphere-oxygen supply pipe (26) that supplies atmosphere gas or oxygen gas into the inside of the kiln (2).

* * * * *